United States Patent [19]

Cotteret

[11] Patent Number: 5,518,505
[45] Date of Patent: May 21, 1996

[54] COMPOSITIONS AND METHODS FOR THE DYEING OF KERATINOUS FIBERS WITH OXIDATION DYE PRECURSORS, INDOLE DERIVATIVE COUPLERS AND OXIDIZING AGENTS

[75] Inventor: Jean Cotteret, Verneuil-sur-Seine, France

[73] Assignee: L'Oreal, Paris, France

[21] Appl. No.: 289,590

[22] Filed: Aug. 15, 1994

Related U.S. Application Data

[63] Continuation of Ser. No. 822,913, Jan. 21, 1992, abandoned.

[30] Foreign Application Priority Data

Jan. 21, 1991 [FR] France ................... 91 00640

[51] Int. Cl.⁶ ....................................... A61K 7/13
[52] U.S. Cl. .................... 8/409; 8/406; 8/407; 8/408; 8/410; 8/423
[58] Field of Search ................. 8/406, 405, 408, 8/409, 410, 414, 416, 423, 429, 407; 424/70

[56] References Cited

U.S. PATENT DOCUMENTS

| | | | |
|---|---|---|---|
| 2,934,396 | 4/1960 | Charle et al. ................. | 8/11 |
| 4,013,404 | 3/1977 | Parent et al. ................. | 8/11 |
| 4,213,960 | 7/1980 | Grollier et al. .............. | 8/405 |
| 4,808,190 | 2/1989 | Grollier et al. .............. | 8/423 |
| 4,888,027 | 12/1989 | Grollier et al. .............. | 8/423 |
| 5,011,500 | 4/1991 | Grollier et al. .............. | 8/410 |
| 5,021,066 | 6/1991 | Aeby et al. .................. | 8/408 |
| 5,021,067 | 6/1991 | Grollier et al. .............. | 8/409 |
| 5,073,174 | 12/1991 | Vayssie et al. ............... | 8/406 |
| 5,096,455 | 3/1992 | Grollier ...................... | 8/410 |
| 5,114,429 | 5/1992 | Junino et al. ................ | 8/410 |
| 5,131,911 | 7/1992 | Lang et al. .................. | 8/405 |
| 5,137,538 | 8/1992 | Madrange et al. ............. | 8/410 |

FOREIGN PATENT DOCUMENTS

| | | |
|---|---|---|
| 2626771 | 8/1989 | France. |
| 2211517 | 7/1989 | United Kingdom. |
| 2213169 | 8/1989 | United Kingdom. |

OTHER PUBLICATIONS

*The Chemistry of Synthetic Dyes*, vol. V, K. Venkataraman, 1971, pp. 478–481.

Primary Examiner—Paul Lieberman
Assistant Examiner—Caroline L. Dusheck
Attorney, Agent, or Firm—Cushman Darby & Cushman

[57] ABSTRACT

Compositions for the oxidative dyeing of keratinous fibers comprising an indole derivative corresponding to the formula (I):

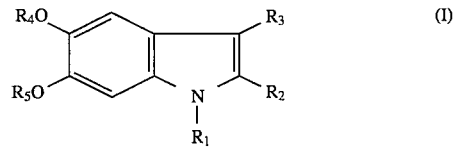

in which:

$R_1$ denotes a hydrogen atom or a $C_1$-$C_4$ alkyl group, $R_2$ and $R_3$ denote a hydrogen atom or a $C_1$-$C_4$ alkyl group or a carboxyl or $C_1$-$C_4$ alkoxycarbonyl group, $R_4$ and $R_5$, which are identical or different, denote a $C_1$-$C_4$ alkyl group, a $C_2$-$C_{20}$ acyl group, an aryl group, or else $R_4$ and $R_5$, together with the oxygen atoms and the two carbon atoms to which they are attached, form a ring optionally containing a carbonyl group or a methylene group unsubstituted or substituted by one or two alkyl or alkoxy or alkylamino groups, it being possible for $R_4$ and $R_5$ simultaneously to denote hydrogen, and the addition salts of inorganic or organic acids, as well as the corresponding alkali, alkaline-earth metal or amine salts, as a coupler, para and/or ortho oxidation dye precursors, and an oxidizing agent.

15 Claims, No Drawings

COMPOSITIONS AND METHODS FOR THE DYEING OF KERATINOUS FIBERS WITH OXIDATION DYE PRECURSORS, INDOLE DERIVATIVE COUPLERS AND OXIDIZING AGENTS

This is a continuation of application Ser. No. 07/822,913, filed Jan. 21, 1992, now abandoned.

The present invention relates to the use of indole derivatives as couplers for dyeing keratinous fibers and in particular for dyeing human hair, and to the compositions and to the dyeing processes used.

It is known to dye keratinous fibers, in particular human hair, with dyeing compositions containing precursors of oxidation dyes and in particular p-phenylenediamines and ortho- or para-aminophenols, generally called "oxidation bases".

It is also known that it is possible to vary the shades obtained with these oxidation bases by combining them with couplers which are also called color modifiers, generally chosen from aromatic meta-diamines, meta-aminophenols and meta-diphenols.

In the field of hair dyeing there is a requirement for oxidation dye precursors or couplers making it possible to impart to the hair, in an oxidizing medium, a color which has a satisfactory resistance to light, to washing, to inclement weather and to perspiration.

The applicant has just found, and this is what forms the subject matter of the invention, that the use of 5,6-dihydroxyindole or of some of its derivatives as couplers, with oxidation dye precursors, makes it possible to obtain, after application to keratinous fibers and in particular to human hair, colors of very varied shades exhibiting particularly remarkable resistance to light, washing, inclement weather and perspiration, epecially when they are employed with p-phenylenediamine and its derivatives. In addition, these dyes do not stain the scalp.

A subject of the invention consists, therefore, of this use.

Another subject of the invention is oxidation dye compositions intended to be employed for dyeing keratinous fibers, in which the indole derivatives defined hereinafter act as couplers, and containing at least one oxidation dye precursor of the para and/or ortho type and at least one oxidizing agent.

The present invention provides, therefore, a dye composition intended to be employed for dyeing keratinous fibers, which contains a reaction product of at least one indole derivative defined hereinafter as a coupler and at least one oxidation dye precursor of the para and/or ortho type in at least one oxidizing agent as defined hereinafter.

Another subject of the invention consists of the process for dyeing keratinous fibers, in particular human hair, using this coupler.

Other subjects of the invention will emerge on reading the description and the examples which follow.

The indole compounds employed as couplers in the oxidation dyeing of keratinous fibers and in particular of human hair, in the presence of at least one para and/or ortho oxidation dye precursor, correspond to the formula:

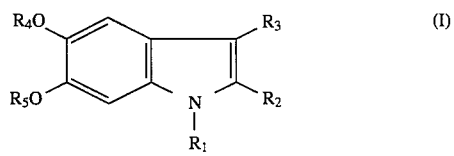

(I)

in which:

$R_1$ denotes a hydrogen atom or a $C_1$-$C_4$ alkyl group, $R_2$ and $R_3$, which are identical or different, denote a hydrogen atom or a $C_1$-$C_4$ alkyl group or a carboxyl or $C_1$-$C_4$ alkoxycarbonyl group, $R_4$ and $R_5$, which are identical or different, denote a $C_1$-$C_4$ alkyl group, a $C_2$-$C_{20}$ acyl group, an aryl group, or else $R_4$ and $R_5$, together with the oxygen atoms and the two carbon atoms to which they are attached, form a ring optionally containing a carbonyl group or a methylene group unsubstituted or substituted by one or two alkyl or alkoxy or alkylamino groups, it being possible for $R_4$ and $R_5$ simultaneously to denote hydrogen, and the addition salts of inorganic or organic acids, as well as the corresponding alkali, alkaline-earth metal or amine salts.

Among the compounds of formula (I) the preferred compounds are the compounds in which the alkyl radical denotes methyl or ethyl, the alkoxycarbonyl radical denotes methoxy or ethoxycarbonyl, and the acyloxy radical denotes acetoxy or tetradecanoyloxy.

Among the preferred compounds of (I) there may be mentioned 5,6-dihydroxyindole, 2-methyl-5,6-dihydroxyindole, 3-methyl-5,6-dihydroxyindole, 2,3-dimethyl-5,6-dihydroxyindole, 1,2-dimethyl-5,6-dihydroxyindole, 2-ethoxycarbonyl- 5,6-dihydroxyindole, 2,3-dimethyl-5,6-dimethoxyindole, 5,6-dimethoxyindole, 5-methoxy-6-acetoxyindole, 5,6-dibenzyloxyindole and 2-carboxy-5,6-dihydroxyindole.

The dye precursors of para or ortho type are compounds which are not themselves dyes but which form a dye by a process of oxidative condensation, either with themselves or in the presence of a coupler or modifier.

These compounds contain functional groups, either two amino groups or an amino group and a hydroxyl group in para or ortho position, relative to each other.

The precursors of para type are chosen in particular from para-phenylenediamines, para-aminophenols, heterocyclic para precursors such as 2,5-diaminopyridine, 2-hydroxy-5-aminopyridine, tetraaminopyrimidine, 4,5-diamino- 1-methylpyrazole, 2-dimethylamino-4,5,6-triaminopyridimidine and the so-called "double" bases.

By way of para-phenylenediamines there may be mentioned the compounds corresponding to the formula (II) below:

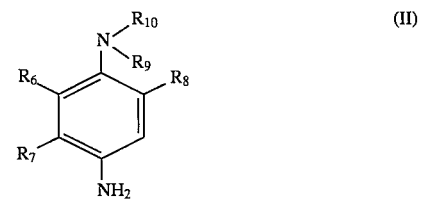

(II)

in which:

$R_6$, $R_7$ and $R_8$, which are identical or different, denote a hydrogen or halogen atom, an alkyl radical containing 1 to 4 carbon toms, or an alkoxy radical containing 1 to 4 carbon atoms, $R_9$ and $R_{10}$, which are identical or different, denote a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, morpholinoalkyl or phenyl radical optionally substituted by an amino group in the para position, these alkyl or alkoxy groups containing from 1 to 4 carbon atoms, or else $R_9$ and $R_{10}$, together with the nitrogen atom to which they are bonded, form a piperidino or morpholino heterocylic ring, provided that $R_6$ and $R_8$ denote a hydrogen atom when $R_9$ and $R_{10}$ do not denote a hydrogen atom, and the salts of these compounds.

Among the compounds of formula (II) there may be mentioned more particularly p-phenylenediamine, p-tolylenediamine, methoxy-para-phenylenediamine, chloro-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 3-methyl- 4-amino-N,N-diethylaniline, N,N-di(β-hydroxyethyl)-para-phenylenediamine, 3-methyl-4-amino-N,N-di(β-hydroxyethyl)aniline, 3-chloro-4-amino-N,N-di(β-hydroxyethyl)aniline, 4-amino-N,N-(ethyl,carbamylmethyl)aniline, 3-methyl-4-amino-N,N-(ethyl, carbamylmethyl)aniline, 4-amino-N,N-(ethyl,β-piperidinoethyl)aniline, 3-methyl-4-amino-N,N-(ethyl,β-piperidinoethyl)aniline, 4-amino-N,N-(ethyl,β-morpholinoethyl)aniline, 3-methyl-4-amino-N,N-(ethyl,β-morpholinoethyl)aniline, 4-amino-N,N-(ethyl,β-acetylaminoethyl)aniline, 4-amino-N-(β-methoxyethyl)aniline, 3-methyl-4-amino-N,N-(ethyl,β-acetylaminoethyl)aniline, 4-amino-N,N-(ethyl,β-mesylaminoethyl)aniline, 3-methyl- 4-amino-N,N-(ethyl,β-mesylaminoethyl)aniline, 4-amino-N,N-(ethyl,β-sulphoethyl)aniline, 3-methyl-4-amino-N,N-(ethyl,β -sulphoethyl)aniline, N-[(4'-amino)phenyl]morpholine, N-[(4'-amino)phenyl]piperidine, 2-hydroxyethyl-para-phenylenediamine, fluoro-para-phenylenediamine, carboxy-para-phenylenediamine, sulpho-para-phenylenediamine, 2-isopropyl-para-phenylenediamine, 2-n-propyl-para-phenylenediamine, hydroxy-2-n-propyl-para-phenylenediamine, 2-hydroxymethyl-para-phenylenediamine, N,N-dimethyl- 3-methyl-para-phenylenediamine, N,N-(ethyl,β-hydroxyethyl)-para-phenylenediamine, N-(dihydroxypropyl)para-phenylenediamine, N-4'-aminophenyl-para-phenylenediamine and N-phenyl-para-phenylenediamine.

These oxidation dye precursors of para type may be introduced into the dye composition either in the form of a free base or in the form of salts such as hydrochloride, hydrobromide or sulphate.

Among the p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-aminomethyl- 4-aminophenol and 2-β-hydroxyethylaminomethyl-4-aminophenol.

The oxidation dyes of ortho type are chosen from ortho-aminophenols such as 1-amino-2-hydroxybenzene, 6-methyl- 1-hydroxy-2-aminobenzene, 4-methyl-1-amino-2-hydroxybenzene and ortho-phenylenediamines.

The so-called double bases are bisphenylenealkylenediamines corresponding to the formula:

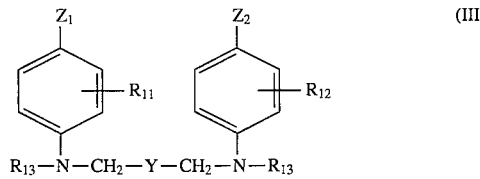

(III)

in which:

$Z_1$ and $Z_2$, which are identical or different, denote hydroxyl or $NHR_{14}$ groups where $R_{14}$ denotes a hydrogen atom or a lower alkyl radical, $R_{11}$ and $R_{12}$, which are identical or different, denote either hydrogen atoms or halogen atoms or else alkyl groups, $R_{13}$ denotes a hydrogen atom or an alkyl, hydroxyalkyl or aminoalkyl group in which the amino residue may be substituted by one or two alkyl groups, Y denotes a radical chosen from the following radicals: $—(CH_2)_n—$, $(CH_2)_m—O—(CH_2)_m—$, $—(CH_2)_m—CHOH—(CH_2)_m$,

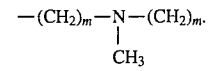

n is an integer between 0 and 8 and m an integer between 0 and 4, it being possible for this so-called double base to be in the form of its addition salts with acids.

The alkyl or alkoxy radicals preferably denote a group containing 1 to 4 carbon atoms and especially methyl, ethyl, propyl, methoxy or ethoxy.

Among the compounds of formula (III) there may be mentioned N,N'-bis(β-hydroxyethyl)-N,N'-bis(4'-aminophenyl)- 1,3-diamino-2-propanol, N,N'-bis(β-hydroxyethyl)-N,N'-bis( 4'-aminophenyl)ethylenediamine, N,N'-bis(4-aminophenyl)tetramethylenediamine, N,N'-bis(β-hydroxyethyl)-N,N'-bis( 4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine.

In addition to the indole coupler of formula (I) defined above it is also optionally possible to employ other couplers which are known per se, such as meta-diphenols, meta-aminophenols, meta-phenylenediamines, meta-acylaminophenols, meta-ureidophenols, meta-carbalkoxyaminophenols, α-naphthol, couplers containing an active methylene group, such as β-ketonic compounds and pyrazolones, and heterocyclic couplers or 4-hydroxyindole and 6- or 7-hydroxyindole.

Among these couplers there may be mentioned more particularly 2,4-dihydroxyphenoxyethanol, 2,4-dihydroxyanisole, meta-aminophenol, resorcinol monomethyl ether, 2-methyl-5-N-(β-hydroxyethyl)aminophenol, 2-methyl-5-N-(β -mesylaminoethyl)aminophenol, 6-hydroxybenzomorpholine, 2,4-diaminoanisole, 2,4-diaminophenoxyethanol, 6-amino-benzomorpholine, [2-N-(β-hydroxyethyl)amino-4-amino]phenoxyethanol, 2-amino-4-N-(β-hydroxyethyl)aminoanisole, (2,4-diamino)phenyl β,γ-dihydroxypropyl ether, 2,4-diaminophenoxyethylamine, 1,3-dimethoxy-2,4-diamino-benzene, 2-methyl-5-aminophenol, 2,6-dimethyl-3-amino-phenol, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, resorcinol, 6-methoxy-3-hydroxyethylaminoaniline, 1-ethoxy-2-bis(β-hydroxyethyl)amino- 4-aminobenzene, 3-diethylaminophenol, 1,3-dihydroxy-2-methylbenzene, 1-hydroxy-2,4-dichloro-3-aminobenzene, 4,6 -hydroxyethoxy-1,3-diaminobenzene, 4-methyl- 6-ethoxy-1,3-diaminobenzene, 4-chloro-6-methyl-3-aminophenol, 6-chloro-3-trifluoroethylaminophenol and their salts.

Direct dyes such as azo or anthraquinone dyes or nitro derivatives of the benzene series may also be used together with the abovementioned compounds, as is well known in the state of the art, especially with a view to shading or enriching in glints the colors provided by the oxidation dye precursors and the coupler of formula (I).

When using the coupler of formula (I) in accordance with the invention, no use is made together with these couplers of any quinone derivative from the class of benzoquinones and naphthoquinones capable of oxidizing the compound of formula (I), nor of any iodide ions in a quantity liable to oxidize the compound of formula (I) and the oxidation dye precursor in the presence of the coupler.

The oxidizing agent is preferably chosen from hydrogen peroxide, urea peroxide, alkali metal bromates, persalts such as perborates and persulphates, hydrogen peroxide being particularly preferred.

The abovementioned indole coupler of formula (I) is used as a coupler in oxidation dye compositions containing, in a medium which is suitable for dyeing, in addition at least one para and/or ortho oxidation dye precursor and optionally other couplers and direct dyes mentioned and at least one oxidizing agent.

These compositions must not contain any iodide ion in proportions liable to oxidize the oxidation dye precursor and the coupler of formula (I).

The dye compositions which form another subject of the invention are essentially characterized in that they contain, in a medium suitable for dyeing:

a) at least one coupler of formula (I)
b) at least one para and/or ortho oxidation dye precursor chosen from para-aminophenols, heterocylic precursors, ortho-aminophenols, ortho phenylenediamines, so-called "double" bases as defined above and paraphenylenediamines corresponding to the formula (IV):

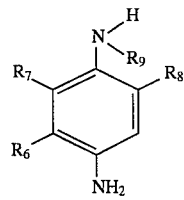

in which:

$R_6$, $R_7$ and $R_8$, which are identical or different, denote a hydrogen or halogen atom, an alkyl radical containing from 1 to 4 carbon atoms or an alkoxy radical containing from 1 to 4 carbon atoms, $R_9$ denotes a hydrogen atom or an alkyl, carbamylalkyl, mesylaminoalkyl, acetylaminoalkyl, ureidoalkyl, carbalkoxyaminoalkyl, piperidinoalkyl or morpholinoalkyl radical, these alkyl or alkoxy groups containing from 1 to 4 carbon atoms, and the salts of these compounds.

Among the compounds of formula (IV) there may be mentioned p-phenylenediamine, p-tolylenediamine, methoxy-para-phenylenediamine, chloro-para-phenylenediamine, 2,6-dimethyl-para-phenylenediamine, 2,5-dimethyl-para-phenylenediamine, 2-methyl-5-methoxy-para-phenylenediamine and 2,6-dimethyl-5-methoxy-para-phenylenediamine.

These oxidation dye precursors of para type may be introduced into the dye composition either in the form of free base or in the form of salts, such as in the form of hydrochloride, hydrobromide or sulphate, and c) at least one oxidizing agent defined above.

These compositions do not contain any iodide ion in quantities liable to oxidize the precursors and the couplers present.

All the oxidation dye precursors of para and/or ortho type and the couplers employed in the dye compositions in accordance with the invention preferably represent from 0.1 to 10% by weight relative to the total weight of the said composition. The concentration of indole compounds of formula (I) may vary between 0.05 and 3.5% by weight relative to the total weight of the composition.

The pH of the composition applied to keratinous fibers, in particular to hair, has a value which is generally between 3 and 11.

This pH is adjusted by employing acidifying or alkalifying agents which are well known in the field of hair dyeing.

In their preferred form of embodiment, the dye compositions in accordance with the invention generally contain anionic, cationic, nonionic or amphoteric surface-active agents or mixtures thereof. Among these surface-active agents there may be mentioned alkylbenzenesulphonates, alkylnaphthalenesulphonates, sulphates, ether sulphates and fatty alcohol sulphonates, quaternary ammonium salts such as trimethylcetylammonium bromide and cetylpyridinium bromide, optionally oxyethylenated fatty acid ethanolamides, polyoxyethylenated acids, alcohols or amines, polyglycerolated alcohols, polyoxyethylenated or polyglycerolated alkylphenols and polyoxyethylenated alkyl sulphates.

These surface-active agents are present in the compositions employed in accordance with the invention in proportions of between 0.5 and 55% by weight and preferably between 2 and 50% by weight, relative to the total weight of the composition.

These compositions may also contain organic solvents to solubilize the compounds which might not be sufficiently soluble in water.

As examples of these solvents there may be mentioned $C_1$-$C_4$ lower alkanols such as ethanol and isopropanol, glycerol, glycols or glycol ethers such as 2-butoxyethanol, ethylene glycol, propylene glycol, diethylene glycol monoethyl ether and monomethyl ether and aromatic alcohols such as benzyl alcohol or phenoxyethanol and similar products or mixtures thereof.

The solvents are preferably present in proportions of between 1 and 40% by weight and in particular between 50 and 30% by weight relative to the total weight of the composition.

The thickening agents which may be added to the compositions in accordance with the invention may be chosen from sodium alginate, gum arabic, cellulose derivatives, acrylic acid polymers and xanthan gum. Inorganic thickening agents such as bentonite can also be employed.

These thickening agents are preferably present in proportions of between 0.1 and 5% and in particular between 0.2 and 3% by weight relative to the total weight of the composition.

The antioxidant agents which may be present in the compositions are chosen in particular from sodium sulphite, thioglycolic acid, sodium bisulphite, dihydroascorbic acid, hydroquinone and homogentisic acid. These antioxidant agents are present in the composition in proportions of between 0.05 and 1.5% by weight relative to the total weight of the composition.

These compositions may also contain other cosmetically acceptable adjuvants such as, for example, penetrating agents, sequestering agents, perfumes, buffers and the like.

The compositions employed in accordance with the invention may be presented in various forms such as in the form of liquids, creams, gels or any other appropriate form for performing a dyeing of keratinous fibers and especially of human hair. These compositions may also be packaged in aerosol bottles in the presence of a propellent agent.

In accordance with the invention, the process consists in applying to the keratinous fibers a composition prepared at the time of use, containing at least one coupler of formula (I), at least one oxidation dye precursor of para type and at least one oxidizing agent other than iodide ions in a quantity which is sufficient to develop a color.

A 20-volume aqueous hydrogen peroxide solution is preferably employed. The mixture obtained is applied to the hair and is left in place for 10 to 40 minutes, preferably 15 to 30 minutes, after which the hair is rinsed, washed with shampoo, rinsed again and dried.

The compounds of formula (I) which are employed preferably when the composition applied to the hair has a pH lower than 9 are 5,6-dihydroxyindole, 2,3-dimethyl- 5,6- dihydroxyindole, 2-methyl-5,6-dihydroxyindole, 3-methyl-5,6-dihydroxyindole, 1,2-dimethyl-5,6-dihydroxyindole, 2-carboxy-5,6-dihydroxyindole, 2-ethoxycarbonyl- 5,6-dihydroxyindole, 5-methoxy-6-acetoxyindole, 5,6-dibenzyloxyindole and 5,6-dimethoxyindole.

When the composition applied to the hair has a pH higher than 9, the indole derivative is preferably a derivative corresponding to the formula:

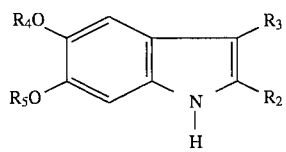

(V)

in which:

$R_2$ denotes hydrogen, alkyl or alkoxycarbonyl, $R_3$ denotes hydrogen or alkyl, $R_4$ and $R_5$, which are identical or different, denote alkyl or acyl, provided that when $R_4$ and $R_5$ denote alkyl, at least one group $R_2$ and $R_3$ is other than hydrogen, it being possible for $R_4$ and $R_5$ together to denote hydrogen.

Among the compounds of formula (V) preference is given to 5,6-dihydroxyindole, 2-ethoxycarbonyl-5,6-dihydroxyindole and 5-methoxy-6-acetoxyindole.

Another form of embodiment of the invention consists in applying separately a composition (A) containing the indole coupler of formula (I) and the oxidation dye precursor, and then, after rinsing, a composition (B) containing the oxidizing agent other than iodide ions.

It is also possible, in accordance with the invention, to apply separately the compositions containing the oxidation dye precursor and then, after rinsing, to apply a composition containing the indole coupler of formula (I) and the oxidizing agent.

The conditions of application and of drying or washing are similar to those indicated above.

The following examples are intended to illustrate the invention without, however, being limiting in character.

EXAMPLES 1 TO 12

Hair dyeing is performed by applying to permanent-waved or natural grey hair containing 90% of white an ad hoc mixture of the dye composition (A) and of the oxidizing composition (B).

This mixture has the pH shown in the tables which follow. This mixture is allowed to act for 30 minutes and the hair is then rinsed and then shampooed. After drying, the hair is dyed to the shade specified at the bottom of the tables which follow.

| in g | 1 | 2 | 3 | 4 | 5 | 6 | 7 | 8 |
|---|---|---|---|---|---|---|---|---|
| A) Dye composition | | | | | | | | |
| 5,6-Dihydroxyindole | 0.447 | | | | | | | |
| 2-Methyl-5,6-dihydroxyindole.HBr | | 0.732 | | | | | | |
| 3-Methyl-5,6-dihydroxyindole | | | 0.489 | | | | | |
| 2-Carboxy-5,6-dihydroxyindole | | | | 0.579 | | | | |
| 5,6-Dimethoxyindole | | | | | 0.532 | | | |
| 2,3-Dimethyl-5,6-dimethoxyindole | | | | | | 0.616 | | |
| 1,2-Dimethyl-5,6-dihydroxyindole | | | | | | | 0.489 | |
| 5-Methoxy-6-acetoxyindole | | | | | | | | 0.615 |
| para-Phenylenediamine | 0.324 | | | 0.324 | | | 0.324 | |
| 2,6-Dimethyl-para-phenylenediamine.2HCl | | 0.657 | | | 0.657 | 0.657 | | 0.657 |
| para-Aminophenol | | | 0.327 | | | | | |
| Monoethanolamine q.s. pH | 9.1 | 8.8 | 9.1 | 8.9 | 8.6 | 9.1 | 9.1 | 8.75 |
| Carrier 2 | X | X | X | X | X | X | X | X |
| Water q.s. | 100 | 100 | 100 | 100 | 100 | 100 | 100 | 100 |
| B) Oxidizing composition | | | | | | | | |
| 20-volume hydrogen peroxide solution | | | | | | | | |
| Phosphoric acid q.s. pH | 1.3 | 1.3 | 1.3 | 1.3 | 1.3 | 1.3 | 1.3 | 1.3 |
| pH w/w mixture A + B | 6.7 | 6.2 | 6.7 | 6.7 | 6.1 | 6.7 | 6.7 | 6.4 |
| Shades obtained on 90% white natural hair | auburn chestnut | matt ashen | coppery golden blonde | natural iridescent mahogany | slightly golden iridescent ashen | golden beige blonde | warm iridescent chestnut | purple-violet light chestnut |

| in g | 9 | 10 | 11 | 12 |
|---|---|---|---|---|
| A) Dye composition | | | | |
| 5,6-Dihydroxyindole | 1.149 | | 0.595 | |
| 2-Ethoxycarbonyl-5,6-dihydroxyindole | | 0.221 | | |
| 5-Methoxy-6-acetoxyindole | | | | 0.41 |
| para-Phenylenediamine | 0.216 | | | 0.216 |
| 2,6-Dimethyl-para-phenylenediamine.2HCl | | | | |
| para-Aminophenol | | | 0.436 | |
| meta-Aminophenol | | 0.109 | | |
| 3-(β-Hydroxyethylamino)-6-methylphenol | 0.167 | | | |
| 2-Methyl-para-phenylenediamine.2HCl | | 0.365 | | |
| α-Naphtol | | 0.144 | | |
| Ethyl alcohol | 30 | | | |
| 20% aqueous ammonia q.s. pH | 11.2 | | | |
| pH | | 10.4 | 10.5 | 10.5 |
| Carrier 1 | | X | X | X |
| Water q.s. | 100 | 100 | 100 | 100 |

| | B) Oxidizing composition | | | | |
|---|---|---|---|---|---|
| | 20-volume hydrogen peroxide solution | | | | |
| | Phosphoric acid q.s. pH | 3 | 3 | 3 | 3 |
| | pH w/w mixture ⅓ A + ⅔ B | 10 | | 10 | 10 |
| | pH w/w mixture A + B | | 9.8 | | |
| | Shades obtained | ashen | subdued | coppery | coppery |
| | on permanent-waved 90% white hair | mahogany | violet | chestnut | mahogany |

COLOR CARRIER 1

| | |
|---|---|
| Octyldodecanol sold by Henkel under the name EUTANOL G ® | 8.0 g |
| Oleic acid | 20.0 g |
| Monoethanolamine lauryl ether sulfate sold by Henkel under the name of SIPON LM 35 ® | 3.0 g |
| Ethyl alcohol | 10.0 g |
| Benzyl alcohol | 10.0 g |
| Cetylstearyl alcohol oxyethylenated with 33 moles of ethylene oxide, sold by Seppic under the name of SIMULSOL GS ® | 2.4 g |
| Ethylenediaminetetraacetic acid | 0.2 g |
| Cationic polymer consisting of repeat units: | 2.2 g |

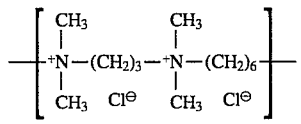

| | |
|---|---|
| Monoethanolamine | 7.5 g |
| Linoleic acid diethanolamide sold by Henkel under the name of COMPERLAN F ® | 8.0 g |
| 20% ammonia | 10.2 g |
| Sodium metabisulphite as 35% aqueous solution | 0.45 g |
| Hydroquinone | 0.15 g |
| 1-Phenyl-3-methyl-5-pyrazolone | 0.2 g |

COLOR CARRIER 2

| | |
|---|---|
| Oleic alcohol polyglycerolated with 2 moles of glycerol | 4.0 g |
| Oleic alcohol polyglycerolated with 4 moles of glycerol | 5.71 g AS |
| Oleic acid | 3.0 g |
| Oleylamine oxyethylenated with 2 moles of ethylene oxide, sold by Akzo under the name ETHOMEEN O 12 | 7.0 g |
| Diethylaminopropyl laurylaminosuccinamate, sodium salt | 3.0 g AS |
| Oleylamine alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as aqueous solution | 0.45 g AS |
| Ammonium acetate | 0.8 g |
| Antioxidant, sequestering agent q.s. | |

I claim:

1. A dye composition for keratinous fibers comprising, in a medium suitable for dyeing said fibers, a reaction product of
at least one oxidation dye precursor; and
at least one coupler having the formula

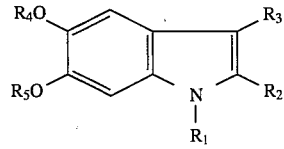

(I)

wherein $R_1$ represents hydrogen or a $C_1$-$C_4$ alkyl group, $R_2$ and $R_3$, each independently, represent hydrogen, $C_1$-$C_4$ alkyl, carboxyl or $C_1$-$C_4$ alkoxycarbonyl, $R_4$ and $R_5$, each independently, represent $C_1$-$C_4$ alkyl, $C_2$-$C_{20}$ acyl or aryl or $R_4$ and $R_5$, together with the oxygen atoms and the two carbon atoms to which they are attached, form a ring optionally containing a carbonyl group or a methylene group unsubstituted or substituted by one or two alkyl, alkoxy or alkylamino groups, it being possible that $R_4$ and $R_5$ are hydrogen simultaneously, an acid addition salt of an inorganic or organic acid, or a corresponding alkali, alkaline earth or amine salt thereof;

said coupler being present in an amount ranging from 0.05 to 3.5 percent by weight based on the total weight of said composition; in at least one oxidizing agent, selected from the group consisting of hydrogen peroxide, urea peroxide, alkali metal bromate and a persalt;

said dye composition not containing iodide ions.

2. The dye composition of claim 1 wherein said coupler of formula (I) is selected from the group consisting of
5,6-dihydroxyindole,
2-methyl-5,6-dihydroxyindole,
3-methyl-5,6-dihydroxyindole,
2,3-dimethyl-5,6-dihydroxyindole,
1,2-dimethyl-5,6-dihydroxyindole,
2-ethoxycarbonyl-5,6-dihydroxyindole,
2,3-dimethyl-5,6-dimethoxyindole,
5,6-dimethoxyindole,
5-methoxy-6-acetoxyindole,
5,6-dibenzyloxyindole and
2-carboxy-5,6-dihydroxyindole.

3. The dye composition of claim 1 wherein said oxidation dye precursor is a para-phenylenediamine of the formula

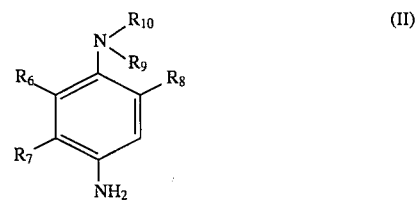

(II)

wherein $R_6$, $R_7$ and $R_8$, each independently, represent hydrogen, halogen, alkyl containing 1–4 carbon atoms or alkoxy containing 1–4 carbon atoms, $R_9$ and $R_{10}$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, morpholinoalkyl or phenyl optionally substituted by amino in the para position, the alkyl or alkoxy moieties containing from 1–4 carbon atoms, or $R_9$ and $R_{10}$, together with the nitrogen atom to which they are attached form a piperidino or morpholino heterocyclic ring, with the proviso that $R_6$ and $R_8$ represent hydrogen when $R_9$ and $R_{10}$ do not represent hydrogen, and a salt thereof.

4. The dye composition of claim 1 wherein said oxidation dye precursor is a bisphenylalkylenediamine of the formula

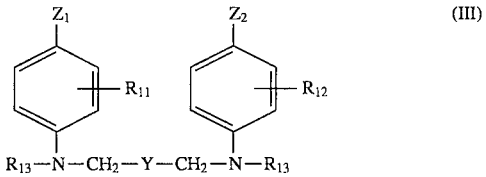

wherein $Z_1$ and $Z_2$, each independently, represent hydroxyl or $NHR_{14}$ wherein $R_{14}$ represents hydrogen or lower alkyl;

$R_{11}$ and $R_{12}$, each independently, represent hydrogen, halogen or alkyl, $R_{13}$ represents hydrogen, alkyl, hydroxyalkyl or aminoalkyl wherein the amino residue optionally is substituted by one or two alkyl groups, Y represents $-(CH_2)_n-$, $-(CH_2)_m-O-(CH_2)_m-$, $-(CH_2)_m-CHOH-(CH_2)_m-$ or

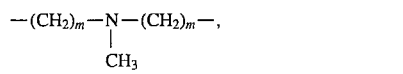

n is an integer ranging from 0 to 8, and m is an integer ranging from 0 to 4, said bisphenylenealkylenediamine optionally being in the form of an acid addition salt.

5. The dye composition of claim 1 which also contains a coupler other than the coupler of formula (I).

6. The dye composition of claim 5 wherein said other coupler is selected from a meta-diphenol, a meta-aminophenol, a meta-phenylene diamine, a meta-acylaminophenol, a meta-ureidophenol, a meta-carbalkoxyaminophenol, α-naphthol, a coupler containing an active methylene group selected from a β-ketonic compound or a pyrazolone, a heterocyclic coupler, 4-hydroxyindole, 6-hydroxyindole or 7-hydroxyindole.

7. The dye composition of claim 1 which also includes a direct dye selected from an azo dye, an anthraquinone dye or a nitro derivative of the benzene series.

8. The dye composition of claim 1 wherein said oxidation dye precursor is a para-phenylenediamine of the formula

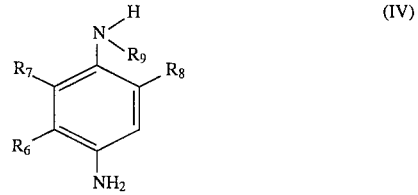

wherein $R_6$, $R_7$ and $R_8$, each independently, represent hydrogen, halogen, alkyl containing 1–4 carbon atoms or alkoxy containing 1–4 carbon atoms, $R_9$ represents hydrogen, alkyl, carbamylalkyl, mesylaminoalkyl, acetylaminoalkyl, ureidoalkyl, carbalkoxyaminoalkyl, piperidinoalkyl or morpholinoalkyl, the alkyl or alkoxy moieties containing from 1–4 carbon atoms, and a salt thereof.

9. The dye composition of claim 8 wherein said para-phenylenediamine of formula (IV) is selected from the group consisting of p-phenylenediamine, p-tolylenediamine, methoxy-para-phenylenediamine, chloro-para-phenylenediamine, 2,6-dimethyl-para-phenylenediamine, 2,5-dimethyl-para-phenylenediamine, 2-methyl-5-methoxy-para-phenylenediamine, and 2,6-dimethyl-5-methoxy-para-phenylenediamine, in the form of a free base or in the form of a salt thereof.

10. The dye composition of claim 1 wherein the pH ranges from 3 to 11.

11. A process for dyeing keratinous fibers comprising applying to said fibers, a fiber dyeing amount of a dye composition comprising, in a medium suitable for dyeing said fibers, a reaction product of
at least one oxidation dye precursor; and
at least one coupler having the formula

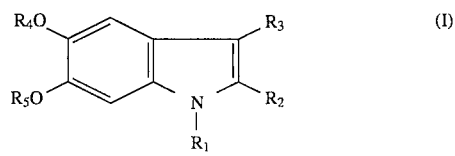

wherein $R_1$ represents hydrogen or a $C_1$-$C_4$ alkyl group, $R_2$ and $R_3$, each independently, represent hydrogen, $C_1$-$C_4$ alkyl, carboxyl or $C_1$-$C_4$ alkoxycarbonyl, $R_4$ and $R_5$, each independently, represent $C_1$-$C_4$ alkyl, $C_2$-$C_{20}$ acyl or aryl or $R_4$ and $R_5$, together with the oxygen atoms and the two carbon atoms to which they are attached, form a ring optionally containing a carbonyl group or a methylene group unsubstituted or substituted by one or two alkyl, alkoxy or alkylamino groups, it being possible that $R_4$ and $R_5$ are hydrogen simultaneously, an acid addition salt of an inorganic or organic acid, or a corresponding alkali, alkaline earth or amine salt thereof;

said coupler being present in an amount ranging from 0.05 to 3.5 percent by weight based on the total weight of said composition; in at least one oxidizing agent, selected from the group consisting of hydrogen peroxide, urea peroxide, alkali metal bromate and a persalt.

12. The process of claim 11 wherein said composition is permitted to remain in contact with said fibers for a period of time ranging from 10 to 40 minutes and thereafter rinsing said fibers, shampooing said fibers, rinsing said fibers and drying said fibers.

13. The process of claim 11 wherein dyeing said fibers is performed at a pH less than 9.

14. The process of claim 11 wherein said coupler is selected from the group consisting of 5,6-dihydroxyindole, 2,3-dimethyl-5,6-dihydroxyindole, 2-methyl-5,6-dihydroxyindole, 3-methyl-5,6-dihydroxyindole, 1,2-dimethyl-5,6-dihydroxyindole, 2-carboxy-5,6-dihydroxyindole, 2-ethoxycarbonyl-5,6-dihydroxyindole, 5-methoxy-6-acetoxyindole, 5,6-dibenzyloxyindole and 5,6-dimethoxyindole.

15. The process of claim 11 wherein dyeing said fibers is performed at a pH higher than 9, and said coupler of formula I, is a coupler having the formula

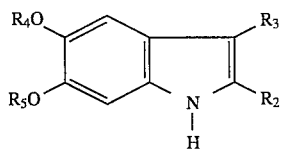

(V)

wherein
- $R_2$ represents hydrogen, alkyl or alkoxycarbonyl,
- $R_3$ represents hydrogen or alkyl,
- $R_4$ and $R_5$, each independently, represent alkyl or acyl,
- with the proviso that when $R_4$ and $R_5$ represent alkyl, at least one of $R_2$ and $R_3$ is other than hydrogen, it being possible for $R_4$ and $R_5$ together to represent hydrogen.

* * * * *